(12) United States Patent  
Matheny

(10) Patent No.: US 9,044,319 B2
(45) Date of Patent: Jun. 2, 2015

(54) ANCHORED CARDIOVASCULAR VALVE

(71) Applicant: Robert Matheny, Norcross, GA (US)

(72) Inventor: Robert Matheny, Norcross, GA (US)

(73) Assignee: Cormatrix Cardiovascular, Inc., Roswell, GA (US)

( * ) Notice: Subject to any disclaimer, the term of this patent is extended or adjusted under 35 U.S.C. 154(b) by 183 days.

(21) Appl. No.: 13/782,024

(22) Filed: Mar. 1, 2013

(65) Prior Publication Data

US 2014/0249623 A1    Sep. 4, 2014

(51) Int. Cl.
*A61F 2/24*    (2006.01)
*A61F 2/92*    (2013.01)

(52) U.S. Cl.
CPC ............. *A61F 2/2418* (2013.01); *A61F 2/92* (2013.01); *A61F 2220/0016* (2013.01); *A61F 2230/0013* (2013.01); *A61F 2250/001* (2013.01)

(58) Field of Classification Search
CPC ... A61F 2/2412; A61F 2/07; A61F 2002/072; A61L 27/3633
USPC .............................. 623/2.13–2.15, 2.17–2.19
See application file for complete search history.

(56) References Cited

U.S. PATENT DOCUMENTS

| 5,522,881 | A  | * | 6/1996  | Lentz     | 623/1.13 |
|-----------|----|---|---------|-----------|----------|
| 7,261,732 | B2 | * | 8/2007  | Justino   | 623/1.24 |
| 8,257,434 | B2 | * | 9/2012  | Matheny   | 623/2.19 |
| 2007/0265699 | A1 | * | 11/2007 | Grewe et al. | 623/1.24 |

* cited by examiner

*Primary Examiner* — Thomas J Sweet
*Assistant Examiner* — Brian Dukert
(74) *Attorney, Agent, or Firm* — Francis Law Group

(57) ABSTRACT

Anchored cardiovascular valves having a support member with at least one leaflet formed therein that is sized and configured to selectively restrict regurgitating blood through the valve, and at least one anchoring mechanism. In a preferred embodiment of the invention, the anchored valves have two anchoring mechanisms, i.e. proximal and distal anchoring mechanisms.

12 Claims, 11 Drawing Sheets

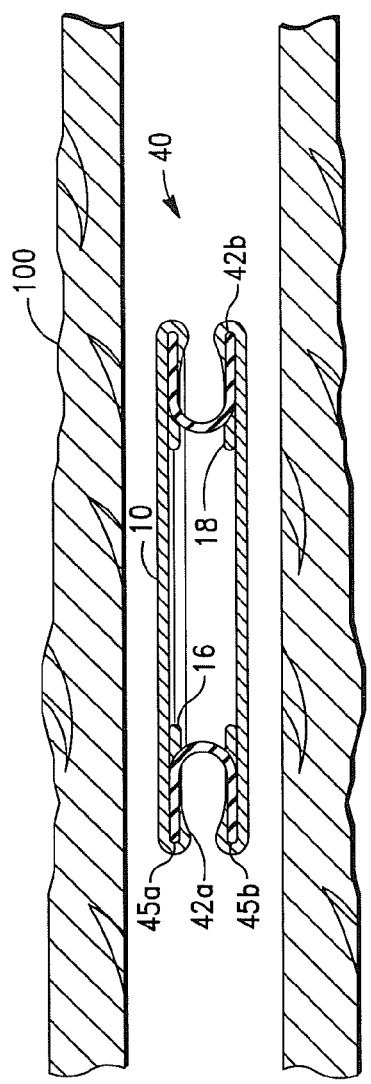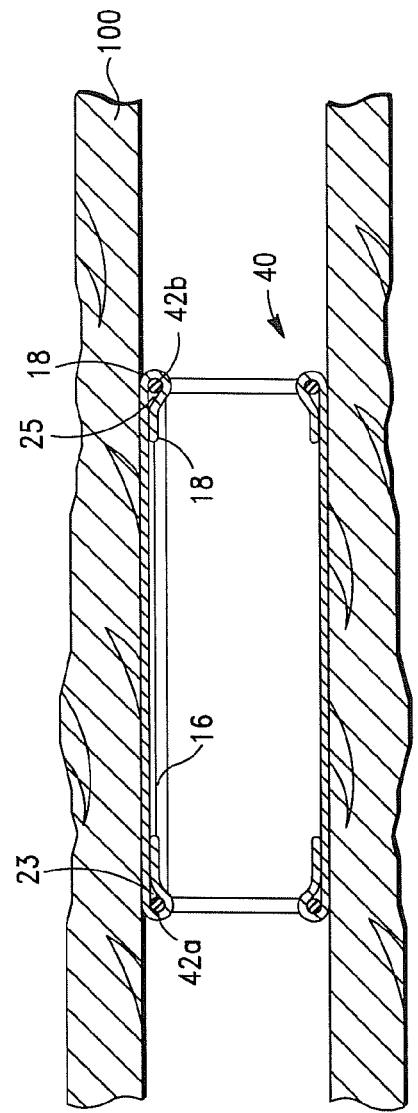

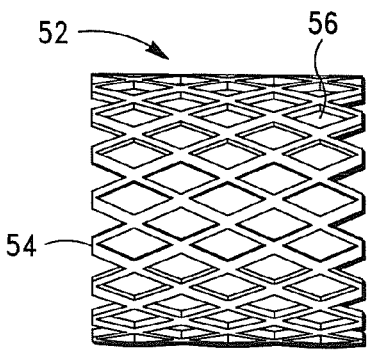
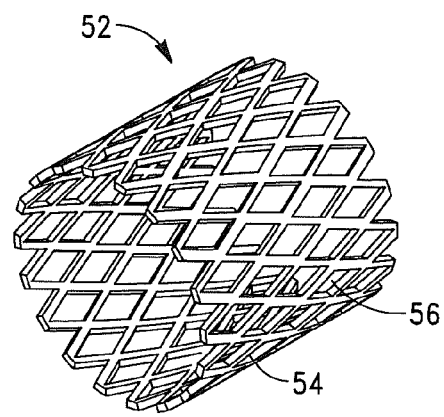
FIG. 16  FIG. 17
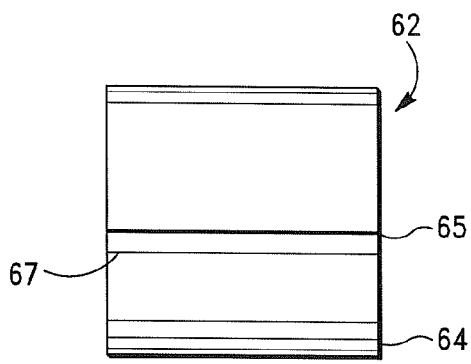
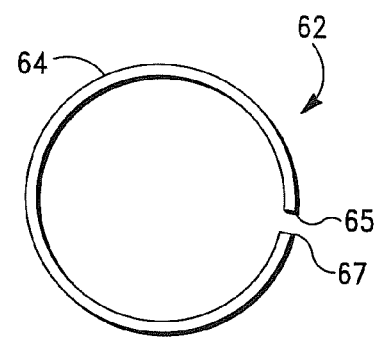
FIG. 19  FIG. 20
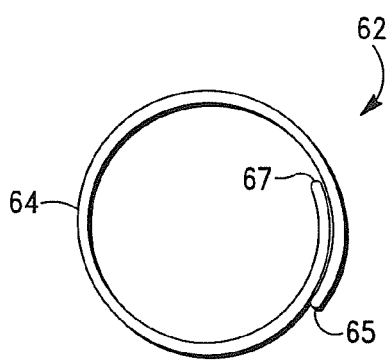
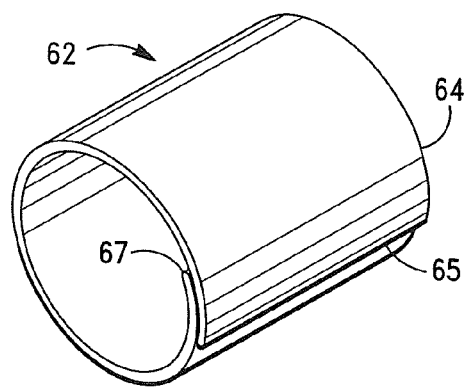
FIG. 21  FIG. 22

ANCHORED CARDIOVASCULAR VALVE

FIELD OF THE INVENTION

The present invention generally relates to prosthetic valves for replacing defective cardiovascular valves. More particularly, the present invention relates to anchored tissue valves for replacing defective aortic, pulmonary, mitral, tricuspid and/or peripheral venous valves.

BACKGROUND OF THE INVENTION

As is well known in the art, the human heart has four valves that control blood flow circulating through the human body. On the left side of the heart is the mitral valve, located between the left atrium and the left ventricle, and the aortic valve, located between the left ventricle and the aorta. Both of these valves direct oxygenated blood from the lungs into the aorta for distribution through the body.

The tricuspid valve, located between the right atrium and the right ventricle, and the pulmonary valve, located between the right ventricle and the pulmonary artery, however, are situated on the right side of the heart and direct deoxygenated blood from the body to the lungs.

The peripheral venous system also includes a number of valves that prevent retrograde blood flow. By preventing retrograde blood flow, the valves found throughout the venous system assist the flow of blood through the veins and returning to the heart.

Normally, the mitral valve has two leaflets and the tricuspid valve has at least two, preferably three leaflets. The aortic and pulmonary valves, however, have normally at least two, preferably three leaflets, also often referred to as "cusps" because of their half-moon like appearance.

Venous valves are usually of the bicuspid type, with each cusp or leaflet forming a reservoir for blood, which, under pressure, forces the free edges of the cusps together to permit mostly antegrade blood flow to the heart. As discussed in detail below, since a majority of venous blood flow is against gravity while a person is standing, incompetent or destroyed venous valves can cause significant medical problems in the legs, ankles, and feet.

Valve diseases are typically classified into two major categories; stenosis and insufficiency. In the case of a stenosis, the native valve does not open properly, whereby insufficiency represents the opposite effect showing deficient closing properties.

Insufficiency of the inlet (atrioventricular) tricuspid valve to the right ventricle of the heart results in regurgitation of blood back into the right atrium, which, serving to receive blood flow returning in the veins from the entire body, then results in turn in suffusion and swelling (edema) of all the organs, most notably in the abdomen and extremities, insufficient forward conduction of blood flow from the right ventricle into the lungs causing compromise of pulmonary function, and ultimately pump failure of the right heart. Collectively these conditions are termed right heart failure, a condition that leads to incapacity and possibly to death if progressive and uncorrected.

Insufficiency of vein function due to the incompetence or destruction of peripheral venous valves leads to acute then chronic swelling of the veins and their dependent lymphatics and tissues. This condition can affect the deep veins of the body, commonly the lower extremities or pelvis, or the superficial veins of the lower extremities in particular, leading to progressive expansion of the veins and further valvular incompetence, a condition known as varicose veins.

Medical conditions like high blood pressure, inflammatory and infectious processes often lead to stenosis and insufficiency. Treatment of heart valve dysfunctions typically include reparation of the diseased heart valve with preservation of the patient's own valve or replacement of the valve with a mechanical or bioprosthetic valve (i.e. "tissue" valve), i.e. a prosthetic valve. Particularly for aortic heart valves, however, it is frequently necessary to introduce a heart valve replacement.

Various prosthetic heart valves have thus been developed for replacement of natural diseased or defective valves. Illustrative are the bioprosthetic "tissue" valves disclosed in Applicant's Co-Pending application Ser. No. 13/560,573.

The implantation of a prosthetic valve, including mechanical valves and bioprosthetic valves, requires a great deal of skill and concentration given the delicate nature of the native cardiovascular tissue and the spatial constraints of the surgical field. It is also critical to achieve a secure and reliable attachment of the valve to host cardiovascular tissue.

Various structures and means have thus been developed to provide a secure and reliable attachment of a prosthetic valve to host cardiovascular tissue. Most surgical techniques comprise suturing the ends of the valve to the annulus of the cardiovascular vessel.

There are numerous drawbacks and disadvantages associated with suturing a valve to host tissue. A major disadvantage is the high risk of perivalvular leakage.

In application Ser. No. 13/560,573 the tissue valve includes a sewing ring that can be employed to suture the ends of the valve to the annulus of the cardiovascular vessel. Although the use of a sewing ring to secure the valve to a cardiovascular vessel can be, and most times is, highly effective, success of the technique is still highly dependent on the skill of the surgeon.

Unfortunately, due to spatial constraints and the delicate nature of the venous system, to date, repair and/or replacement of peripheral venous valves have garnered limited success. Thus, insufficiency of vein function due to the incompetence or destruction of peripheral venous valves is typically treated conservatively with manual compression lymphatic massage therapy, skin lubrication, sequential compression pump, ankle pump, compression stockings, blood pressure medicine, and frequent periods of rest elevating the legs above the heart level.

There is thus a need to provide prosthetic tissue valves that provide secure, reliable and consistent attachment to cardiovascular vessels.

There is also a need to provide improved prosthetic tissue valves to replace diseased or defective peripheral venous valves.

It is therefore an object of the present invention to provide prosthetic tissue valves that provide secure, reliable, and consistently highly effective attachment to cardiovascular vessels for a predetermined period of time.

It is another object of the present invention to provide improved prosthetic tissue valves to replace diseased or defective peripheral venous valves It is another object of the present invention to provide prosthetic tissue valves that substantially reduce or eliminate intimal hyperplasia after intervention in a vessel and the harsh biological responses associated with conventional polymeric and metal valves.

It is another object of the present invention to provide prosthetic tissue valves having optimum mechanical compatibility with vascular structures.

SUMMARY OF THE INVENTION

The present invention is directed to anchored cardiovascular valves having a support member with at least one leaflet formed therein that is sized and configured to selectively restrict regurgitating blood through the valve, and at least one anchoring mechanism. In a preferred embodiment of the invention, the anchored valves have two anchoring mechanisms, i.e. proximal and distal anchoring mechanisms.

The support member and anchoring mechanisms (hereinafter "anchored valve" or "anchored tissue valve") are capable of transitioning from a pre-deployment configuration, wherein the anchored valve is capable of being positioned within a cardiovascular vessel, to a post-deployment configuration, wherein the valve is disposed proximate host tissue of the vessel.

In a preferred embodiment of the invention, the support member comprises an extracellular matrix (ECM) material. According to the invention, the ECM material can be derived from various mammalian tissue sources including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

The ECM material can also be derived from other sources, including, without limitation, collagen from plant sources and synthesized extracellular matrices, i.e. cell cultures.

In some embodiments of the invention, the ECM support member includes at least one pharmacological agent, i.e. an agent that is capable of producing a desired biological effect in vivo, e.g., stimulation or suppression of cell division, stimulation or suppression of apoptosis, stimulation or suppression of an immune response, anti-bacterial activity, etc.

In some embodiments of the invention, the anchoring mechanisms comprise reinforcing rings or bands that are positioned and secured at desired positions, e.g. proximal and distal ends, on or in a valve.

In some embodiments, the anchoring mechanisms comprise a microneedle anchoring mechanisms having a plurality of biodegradable microneedles or barbs that are adapted to maintain contact of the anchored valve against the wall of a vascular structure when disposed therein.

In a preferred embodiment of the invention, the anchoring mechanisms comprise expandable anchoring mechanisms or anchors.

According to the invention, the anchoring mechanisms can comprises various materials, preferably biocompatible materials, such as biocompatible metals, e.g., Nitinol® and stainless steel, and various polymeric materials. The anchoring mechanisms can also comprise various biodegradable materials, such as magnesium and ECM material.

The microneedle anchoring mechanisms can also comprise a pharmacological or active agent (i.e. drug), e.g., Heparin®, Plavix®, etc., or a combination thereof.

In some embodiments of the invention, the metal anchoring mechanisms include an immunomodulating compound.

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

In some embodiments of the invention, when the anchored valve includes proximal and distal anchoring mechanisms and the anchoring mechanisms are in a post-deployment configuration, at least the proximal and distal ends of the anchored valve are supported and positioned proximate the wall of a vessel (i.e. host tissue thereof) by the anchoring mechanism for a predetermined temporary anchor support time period.

In some embodiments of the invention, wherein the support member comprises an ECM material, the anchor support time period is within the process of tissue regeneration.

In some embodiments of the invention, the anchoring mechanisms completely degrade after the anchor support time period.

In some embodiments of the invention, degradation of the anchoring mechanisms is controlled, whereby substantially all of the anchoring mechanism material is absorbed proximate the ECM support member. In some embodiments, the anchoring mechanisms are encased in remodeled tissue.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 14 is a side plan, sectional view of the single-ring anchoring mechanism shown in FIG. 13 disposed in a support member (forming an anchored tissue valve) with the anchoring mechanism and support member in a pre-deployment configuration in a cardiovascular vessel, in accordance with the invention;

FIG. 15 is a side plan, sectional view of the anchored tissue valve shown in FIG. 14 with the anchoring mechanism and support member in a post-deployment configuration in a cardiovascular vessel, in accordance with the invention;

FIG. 16 is a side plan view of one embodiment of an expandable multi-cell anchoring mechanism, in accordance with the invention;

FIG. 17 is a perspective view of the expandable anchoring mechanism shown in FIG. 16, in accordance with the invention;

FIG. 19 is a side plan view of another embodiment of an expandable anchoring mechanism, in accordance with the invention;

FIG. 20 is a front plan view of the anchoring mechanism shown in FIG. 19, in accordance with the invention;

FIG. 21 is a front plan view of the expandable anchoring mechanism shown in FIG. 20 in a pre-deployment configuration, in accordance with the invention;

FIG. 22 is a perspective view of the expandable anchoring mechanism shown in FIG. 21, in accordance with the invention;

DETAILED DESCRIPTION OF THE PREFERRED EMBODIMENT

Figure 1:
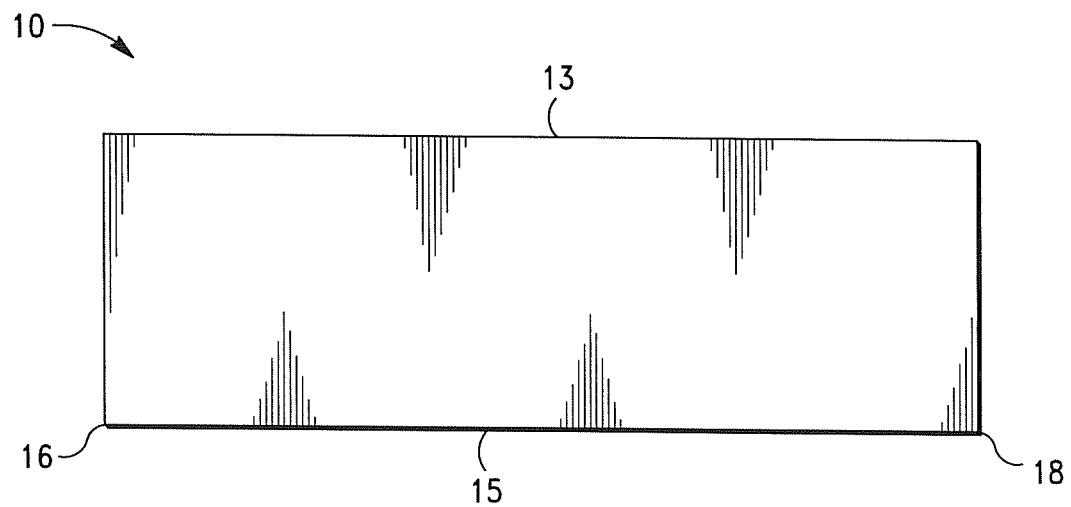
FIG. 1 is a top plan view of one embodiment of a support member in sheet form, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "anchored valve" and "valve" are used interchangeably herein, and mean and include a structure, device or system of the invention that is configured for implantation in a cardiovascular vessel and selective restriction of fluid flow therethrough.

The terms "anchoring mechanism" and "anchor", as used herein in connection with some embodiments of an anchored valve, mean a temporary structure that is configured and employed to "temporarily" position the valve proximate vessel tissue. As discussed in detail herein, in some embodiments of the invention, the anchoring mechanisms are designed and configured to temporarily position tissue valves proximate a recipient's cardiovascular tissue for a predetermined period of time, which, in some embodiments, is preferably within the process of new tissue regeneration.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

According to the invention, ECM material can comprise, in whole or in part, just the basement membrane (or transitional epithelial layer) with the subadjacent tunica propria, the tunica submucosa, tunica muscularis, and tunica serosa. The extracellular matrix component of the ECM material can thus contain any or all of these layers or only the basement membrane portion, excluding the submucosa.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, antiviral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the terms "pharmacological agent", "active agent", "drug" and "active agent formulation" can further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, paraparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues, and antifolates. Chemotherapy drugs can also include, without limitation, plant alkaloids, such as vincristine, vinblastine, vinorelbine, vindesine, podophyllotoxin, etoposide, teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofrofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "cells" and "stem cells" are also used interchangeably herein, and mean and include an organism that has the potential to induce modulating proliferation, and/or growth and/or regeneration of tissue. Stem cells can thus include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

According to the invention, the terms "pharmacological agent", "active agent", "drug" and "active agent formulation" can further include the following active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "active agent formulation", "pharmacological agent formulation" and "agent formulation", are also used interchangeably herein, and mean and include an active agent optionally in combination with one or more pharmaceutically acceptable carriers and/or additional inert ingredients. According to the invention, the formulations can be either in solution or in suspension in the carrier.

The term "pharmacological composition", as used herein, means and includes a composition comprising a "pharmacological agent" and/or a "pharmacological agent formulation" and/or any additional agent or component identified herein.

The term "therapeutically effective", as used herein, means that the amount of the "pharmacological composition" and/or "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a "pharmacological composition" or "pharmacological agent" or "active agent formulation" to biological tissue.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to anchored valves which, in some embodiments, are formed from extracellular matrix materials. According to the invention, the anchored valves of the invention can be readily employed to replace native valves in the body including, without limitation, diseased or defective aortic, pulmonary, mitral, tricuspid and/or peripheral venous valves.

As discussed in detail herein, the anchored valves include a support member having at least one internal leaflet that is sized and configured to selectively prevent undesired regurgitation of blood through the valve, and at least one anchoring mechanism. In a preferred embodiment, the anchored valves include two anchoring mechanisms.

In some embodiments of the invention, the anchoring mechanisms comprise expandable anchoring mechanisms, whereby the support member and expandable anchoring mechanisms, i.e. anchored valve, are capable of transitioning from a pre-deployment configuration, wherein the anchored valve is capable of being positioned within a cardiovascular vessel, to a post-deployment configuration, wherein the anchored valve is disposed proximate host tissue of the vessel.

According to the invention, the support member, which is employed to form the valve structure, can comprise various biocompatible materials, including, without limitation, Dacron, mammalian tissue, e.g., bovine tissue, and other polymeric materials.

In some embodiments of the invention, the support member comprises an extracellular matrix (ECM) material (anchored valves formed therefrom hereinafter referred to as "anchored tissue valves" or "tissue valves").

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornament=extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

According to the invention, ECM material can comprise, in whole or in part, just the basement membrane (or transitional epithelial layer) with the subadjacent tunica propria, the tunica submucosa, tunica muscularis, and tunica serosa. The extracellular matrix component of the ECM material can thus contain any or all of these layers or only the basement membrane portion, excluding the submucosa.

As stated above, in some embodiments of the invention, the ECM support member (or material thereof) includes at least one pharmacological agent or composition, i.e. an agent that is capable of producing a desired biological effect in vivo, such as stimulation or suppression of cell division, stimulation or suppression of apoptosis, stimulation or suppression of an immune response, anti-bacterial activity, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenac, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. Several significant properties and beneficial actions resulting therefrom are discussed in detail below. Additional properties and beneficial actions are set forth in Co-Pending application Ser. No. 13/373,569, filed on Sep. 24, 2012; which is incorporated by reference herein in its entirety.

Anti-Inflammatory Properties/Actions

Statins have numerous favorable effects on vascular wall cells and the cardiovascular system. One specific example is that statins facilitate the reduction of the G-Protein-Coupled Receptor, thromboxane A2 ($TXA_2$), which lowers the platelet activation and aggregation, and augmentation of adhesion molecules and chemokines.

Statins further impact vascular wall cells and the cardiovascular system by blocking ras homilog gene family, member A (RhoA) activation. Blocking RhoA activation further impacts numerous systems, such as macrophage growth, tissue plasminogen activators (t-PA), plasminogen activator inhibitor type 1 (PAI-1), smooth muscle cell (SMC) proliferation, nitric oxide (NO) production, endothelins, and angiotensin receptors.

Macrophage growth reduced by blocking RhoA activation results in the reduction of matrix metalloprotinases (MMPs) and tissue factors (TF). Lowered MMPs also results in a lowered presence of thrombi, as the MMPs attach to ECM present in thrombi or damaged ECM at wound sites.

Fibrinolysis Properties/Actions

Blocking RhoA activation also affects the presence of tissue plasminogen activators (t-PA) and plasminogen activator inhibitor type 1 (PAI-1), which is the principal inhibitor of fibrinolysis. With t-PA presence raised and PAI-1 diminished from the blocking of RhoA activation induced by statins, a reduced thrombotic effect is realized due to reduced opportunity for fibrin to form the polymeric mesh of a hemostatic plug.

NO Regulation Properties/Actions

Blocking RhoA activation also affects the presence of Nitric Oxide (NO) in the cardiovascular system. NO contributes to vessel homeostasis by inhibiting vascular smooth muscle contraction and growth, platelet aggregation, and leukocyte adhesion to the endothelium.

RhoA Activation Blocking Properties/Actions

The administration of statins can also enhance the presence of endothelins and angiotensin receptors. Endothelins and angiotensin receptors can also be affected by the subsequent blocking of RhoA activation associated with statin administration.

There are three isoforms of endothelins; ET-1, ET-2, and ET-3, with ET-1 being the isoform primarily affected by statins and RhoA activation blocking. Secretion of ET-1 from the endothelium signals vasoconstriction and influences local cellular growth and survival.

Angiotensin receptors are protein coupled receptors that are responsible for the signal transduction of the vasoconstricting stimulus of the main effector hormone angiotensin IL Angiotensin Receptor II Type I (AT-1) is the angiotensin receptor primarily affected by statin administration and RhoA activation blocking. AT-1 mediates vasocontraction, cardiac hypertrophy, vascular smooth muscle cell proliferation, inter alia.

C-Reactive Protein Reduction Properties/Actions

C-Reactive Proteins (CRP) are also reduced by statins. CRPs are found in the blood; the levels of which deviate in response to differing levels of inflammation.

Adhesion Molecule Reduction Properties/Actions

Statins also reduce the presence of adhesion molecules on the endothelium. Adhesion molecules are proteins that are located on the cell surface and are involved with inflammation and thrombin formation in vascular endothelial cells.

Rac-1 Reduction Properties/Actions

The expression of Rac-1 is also reduced by statins. Rac-1 is a protein found in human cells, which plays a central role in endothelial cell migration, tubulogenesis, adhesion, and permeability. The decrease in the presence of Rac-1 also results in the decrease of reactive oxygen species (ROS).

According to the invention, the ECM support member (or material) can include 10 mg or greater of a statin to achieve a higher concentration of the statin within a desired tissue, or 10 ug or less to achieve a lower concentration of the statin within a desired tissue.

In some embodiments of the invention, the ECM support member (or material) includes chitosan or a derivative thereof. As also set forth in detail in Co-Pending application Ser. No. 13/573,569, chitosan also exhibits numerous beneficial properties that provide several beneficial biochemical actions or activities.

In some embodiments of the invention, the ECM support member (or material) includes a cell. According to the invention, the cell can comprise, without limitation, a stem cell, such as, for example, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the ECM support member (or material) includes a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

As indicated above, in a preferred embodiment of the invention, the anchored valves of the invention, including anchored tissue valves, further include at least one, more preferably, at least two anchoring mechanisms. According to the invention, the anchoring mechanisms can comprise various forms and materials.

Thus, in some embodiments of the invention, the anchoring mechanisms comprise reinforcing rings or bands that are positioned and secured at desired positions, e.g. proximal and distal ends, on or in a valve. According to the invention, the rings and bands preferably comprise a biocompatible material, such as a biocompatible metal, e.g., Nitinol® and stainless steel, and various polymeric materials. The rings and bands can also comprise various biodegradable materials, such as magnesium and ECM material.

In some embodiments, the anchoring mechanisms comprise expandable anchoring mechanisms.

As defined above and discussed in detail below, the terms "anchoring mechanism" and "anchor", as used in connection with some embodiments of anchored valves of the invention, including anchored tissue valves, mean a structure that is configured and employed to temporarily position a valve of the invention proximate host tissue of a vessel. The function of such an anchoring mechanism of the invention is thus to temporarily support and position a valve of the invention proximate host tissue of a vessel, i.e. vessel wall.

In a preferred embodiment, such anchoring mechanisms temporarily position an anchored "tissue" valve proximate host tissue of a vessel, and maintain contact therewith for a predetermined anchor support period of time within the process of tissue regeneration.

Thus, in some embodiments, when an ECM based anchored valve of the invention is deployed in a vessel, the anchoring mechanisms, e.g. proximal and distal anchoring mechanisms, merely position the ECM support member and, hence, anchored tissue valve formed therefrom proximate host tissue of the vessel (or vessel wall) long enough to initiate blood vessel growth proximate the vessel wall. Once blood vessels begin to grow into the ECM support member and stem cells attach to the surface, an endothelium layer or lining grows across the ECM support member and starts to remodel into healthy, native vascular wall cells and, thereby, creating a remodeled, natural vascular wall.

Applicants have found that, in most instances, the ECM support member will be completely enclosed in an endothelial lining in a minimum time duration of approximately 3-8 weeks and a maximum time duration of approximately 2-6 months.

In a preferred embodiment of the invention, the anchoring mechanisms employed in anchored tissue valves are also completely enclosed in the endothelial lining during tissue remodeling, and remain encased in the endothelial lining for a defined period of time during and post healing.

According to the invention, once the anchoring mechanisms and ECM support member are enclosed in the endothelial lining, the ECM material begins to be reabsorbed during the tissue remodeling (or regeneration) process, and the anchoring mechanisms are no longer required for structural support.

Thus, in a preferred embodiment of the invention, after tissue remodeling commences (i.e. blood vessel growth is initiated), the function of the anchoring mechanisms transitions from a positioning and supporting function, wherein the anchoring mechanisms position and support the ECM support member and, hence, tissue valve proximate the host tissue of the vessel, to a reinforcing function, wherein the anchoring mechanisms merely reinforce the anchored tissue valve and/or remodeled tissue during (and after) the tissue regeneration process.

Preferably, the radial force exerted on the ECM support member and, hence, tissue valve by the anchoring mechanisms is highest at deployment. The radial force then preferably diminishes after approximately eight (8) weeks. After the anchoring mechanisms are completely embedded in the remodeled tissue, the radial force provided by the anchoring mechanisms is minimal, more preferably, zero.

Depending on the material employed to form the anchoring mechanisms, the anchoring mechanisms could be completely absorbed or remain in place to reinforce the valve, i.e. function like a rebar in a matrix.

As stated above, in some embodiments, the anchoring mechanisms comprise expandable anchoring mechanisms. In some embodiments, a first or proximal expandable anchoring mechanism is disposed proximate the proximal end of the valve and a second or distal expandable anchoring mechanism is disposed proximate the distal end of the valve.

In a preferred embodiment of the invention, the proximal and distal anchoring mechanisms are also capable of transitioning from a pre-deployment configuration, wherein a pre-deployment configuration of the support member and, hence, anchored valve formed therefrom is facilitated (or provided), i.e. a configuration that allows the valve to be positioned within a cardiovascular vessel, to a post-deployment configuration, wherein at least the proximal and distal ends of the valve are supported and positioned proximate the wall of the vessel (i.e. host tissue thereof) by the anchoring mechanisms.

In a preferred embodiment of the invention, the proximal and distal anchoring mechanisms preferably comprise a biocompatible material. More preferably, the anchoring mechanisms comprise a biocompatible and biodegradable material.

Thus, in some embodiments, the anchoring mechanisms comprise stainless steel.

In some embodiments, the anchoring mechanisms comprise a cobalt-chrome nickel alloy.

In some embodiments, the anchoring mechanisms comprise magnesium or an alloy thereof.

In some embodiments, the anchoring mechanisms comprise Nitinol®.

In some embodiments of the invention, the metal anchoring mechanisms include a coating of an immunomodulating compound that suppresses acute immune responses, while up regulating chronic immune response (i.e. tissue reconstruction).

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

According to the invention, the anchoring mechanisms can also comprise a polymeric material or a cross-linked ECM material.

As discussed in detail below, in some embodiments of the invention, each anchoring mechanism comprises a single ring or band.

In some embodiments of the invention, the anchoring mechanisms comprise microneedle anchoring mechanisms having a plurality of preferably biodegradable microneedles or barbs that are adapted to maintain contact of the anchored valve against the wall of a vascular structure when disposed therein.

In some embodiments, the microneedles comprise drug-eluting members that facilitate the direct administration of a pharmacological agent to host tissue, e.g. host tissue of a vascular structure.

Referring now to FIGS. 1-9, a first embodiment of an anchored valve of the invention (denoted "11") and methods for forming same will be discussed in detail. In a preferred embodiment of the invention, the anchored valve 11 includes a support member 10 and two anchoring mechanisms (denoted "20a" and "20b" in FIGS. 3 and 8), which, as discussed above, are capable of transitioning from a pre-deployment configuration to a post-deployment configuration.

As indicated above, the support member 10, which is employed to form the valve structure, can comprise various materials, including, without limitation, Dacron and mammalian tissue, e.g., bovine tissue.

In a preferred embodiment, the support member 10 comprises an expandable ECM material that is similarly capable of transitioning from a pre-deployment configuration to facilitate positioning of the support member and, hence, anchored tissue valve formed therefrom, within a cardiovascular vessel, to a post-deployment configuration, wherein the anchored valve is disposed proximate host tissue of the vessel.

In some embodiments of the invention, the support member 10 comprises a single layer of ECM material. In some embodiments, the support member 10 comprises multiple, layers of ECM material.

As stated above, according to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

Figure 2:
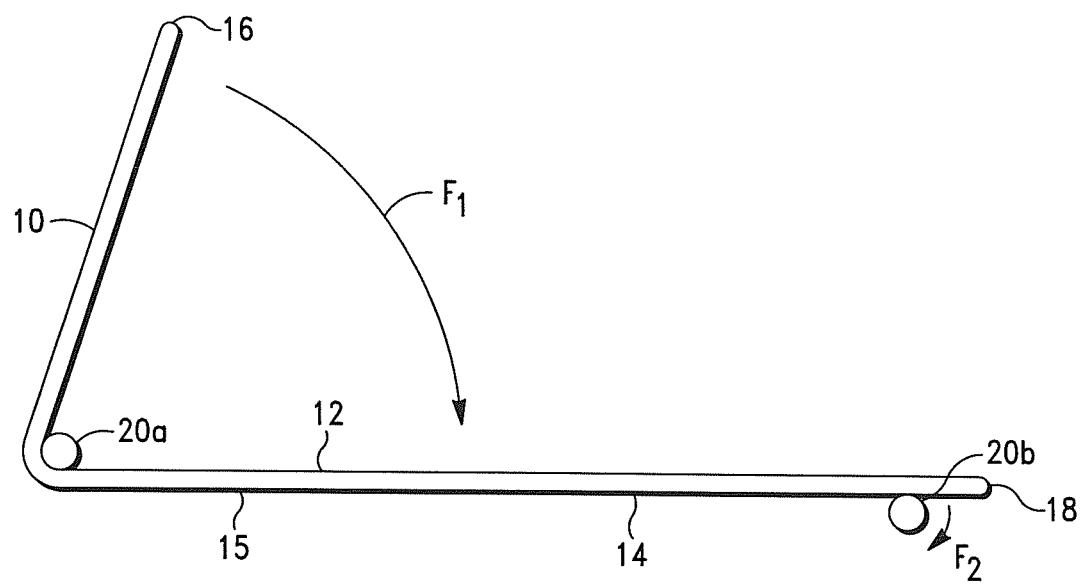
FIG. 2 is a side plan view of the support member shown in FIG. 1 in a partially folded configuration, in accordance with the invention.

Referring now to FIGS. 1 and 2, the support member material 10 is preferably provided in sheet form (hereinafter "ECM sheet" or "ECM support member"). A first anchoring mechanism 20a is disposed on the top surface 12 of the ECM sheet 10 a first distance from a first end 16 of the sheet 10. A second anchoring mechanism 20b is disposed on the bottom surface 14 of the ECM sheet 10 a first distance from the second end 18 of the sheet 10.

Figure 3:
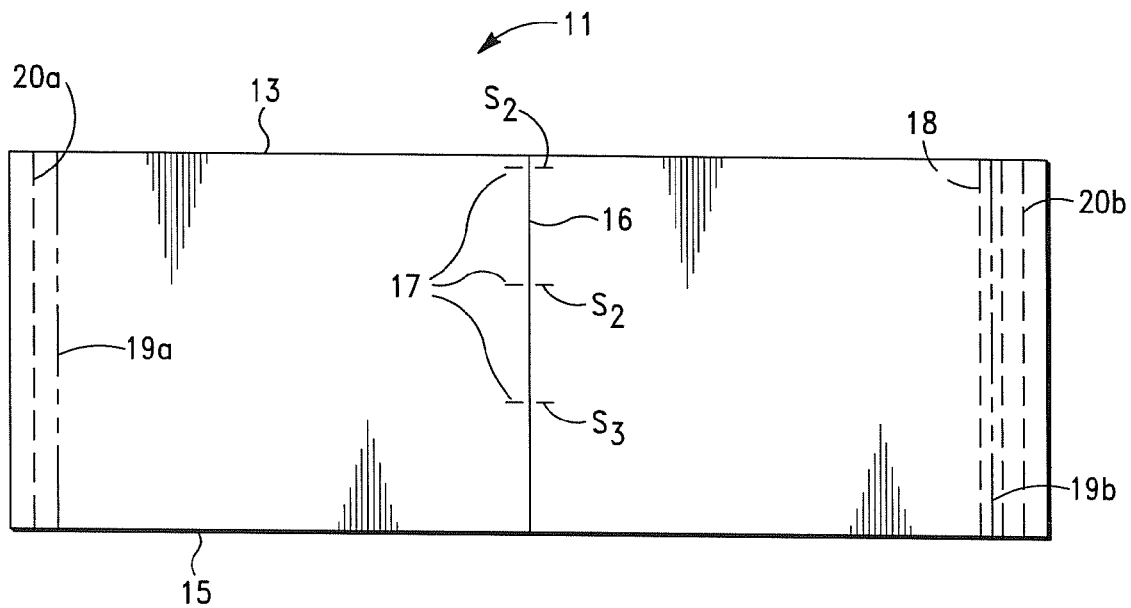
FIG. 3 is a top plan view of the support member shown in FIG. 1 in a fully folded configuration, in accordance with the invention.

As illustrated in FIGS. 2 and 3, the first and second anchoring mechanisms 20a, 20b comprise an elongated material, i.e. a wire or strand. Preferably, the anchoring mechanism material is capable of being formed into a substantially circular shape that conforms to the formed tubular shape of the anchored valve 11 (discussed below).

According to the invention, the first and second anchoring mechanisms 20a, 20b can thus comprise various deformable materials. Preferably, the first and second anchoring mechanisms 20a, 20b comprise a biocompatible material, such as a biocompatible metal, e.g., stainless steel, and various polymeric materials. More preferably, the first and second anchoring mechanisms 20a, 20b comprise a biocompatible and biodegradable material, such as magnesium (or a magnesium alloy) wire (or strand) of cross-linked ECM material.

After the first and second anchoring mechanisms 20a, 20b are positioned on the ECM sheet 10, the first end 16 of the sheet 10 is folded over (as denoted by Arrow "$F_1$"), whereby the first anchoring mechanism 20a is encased in the folded over ECM sheet 10 (or the pocket 23 formed thereby).

Figure 8:
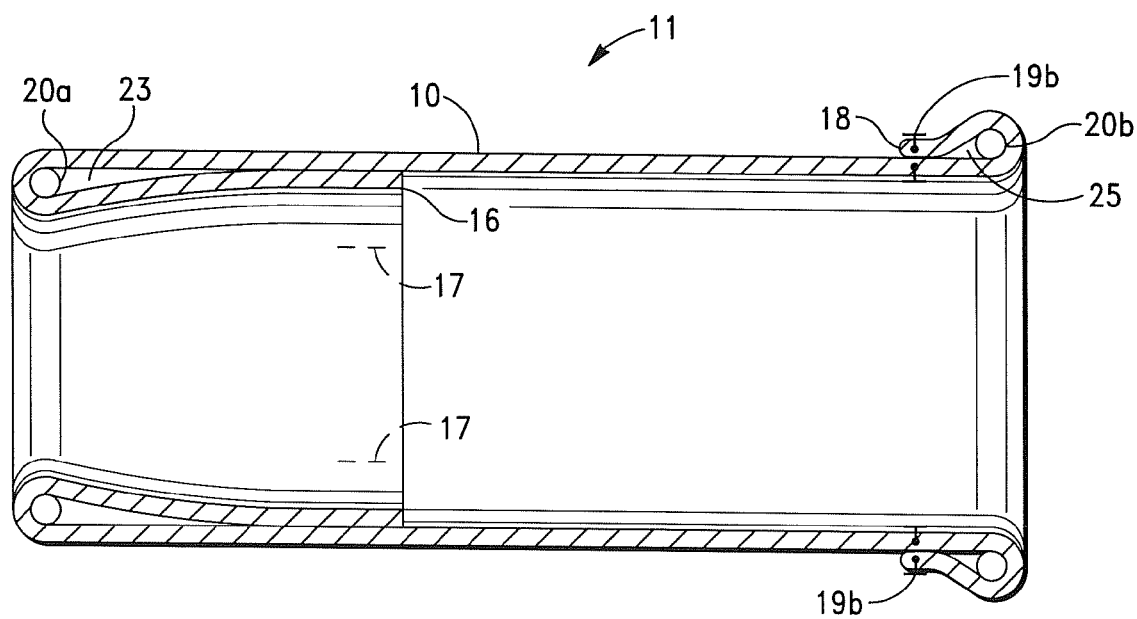
FIG. 8 is a side plan, sectional view of one embodiment of an anchored tissue valve, in accordance with the invention.

In some embodiments of the invention, after the first end 16 of the ECM sheet 10 is folded over, the sheet is sutured (shown in phantom and denoted "19a") proximate the first anchoring mechanism 20a to maintain the position of the anchoring mechanism 20a within the sheet pocket 23 (see FIGS. 3 and 8).

In a preferred embodiment, the second end 18 of the ECM sheet 10 is also folded over outwardly (as denoted by Arrow "$F_2$") to encase the second anchoring mechanism 20b. In an alternative embodiment (not shown), the second end 18 is folded over "inwardly" to encase the second anchoring mechanism 20b.

Referring now to FIG. 3, after the first end 16 of the ECM sheet 10 is folded over, the first end 16 of the sheet 10 is sutured or stitched 17 to the top surface 12 of the sheet 10. In some embodiments, the first end 16 of the ECM sheet 10 is sutured 17 to the top surface 12 at three, preferably, equally spaced positions (denoted "$S_1$", "$S_2$" and "$S_3$") to, as discussed in detail below, form three (3) valve leaflets.

According to the invention, the first end 16 of the ECM sheet 10 can alternatively be sutured to the top surface 12 at two positions to form two (2) valve leaflets, or one position to form one (1) leaflet.

Figure 4:
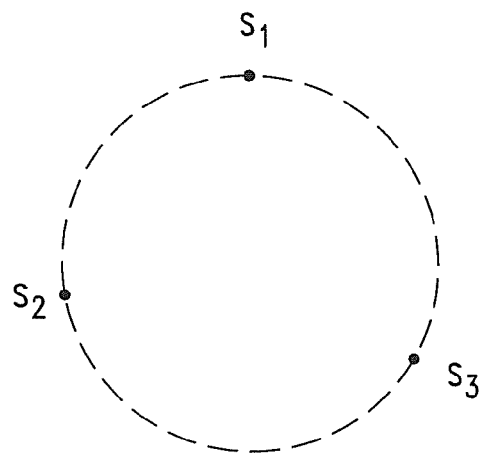
FIG. 4 is a schematic illustration of one embodiment of the support member internal suturing points, in accordance with the invention.

When the ECM sheet 10 is rolled to faun a tubular structure (as discussed in detail below), the suture positions $S_1$, $S_2$ and $S_3$ are preferably disposed approximately 120° apart (see FIG. 4).

After the second end 18 of the ECM sheet 10 is folded over, the second end 18 of the sheet 10 is sutured or stitched 19b to the bottom surface 14 of the sheet 10. According to the invention, the sutures 19b can comprise spaced (or intermittent) sutures or a continuous suture.

Figure 5:
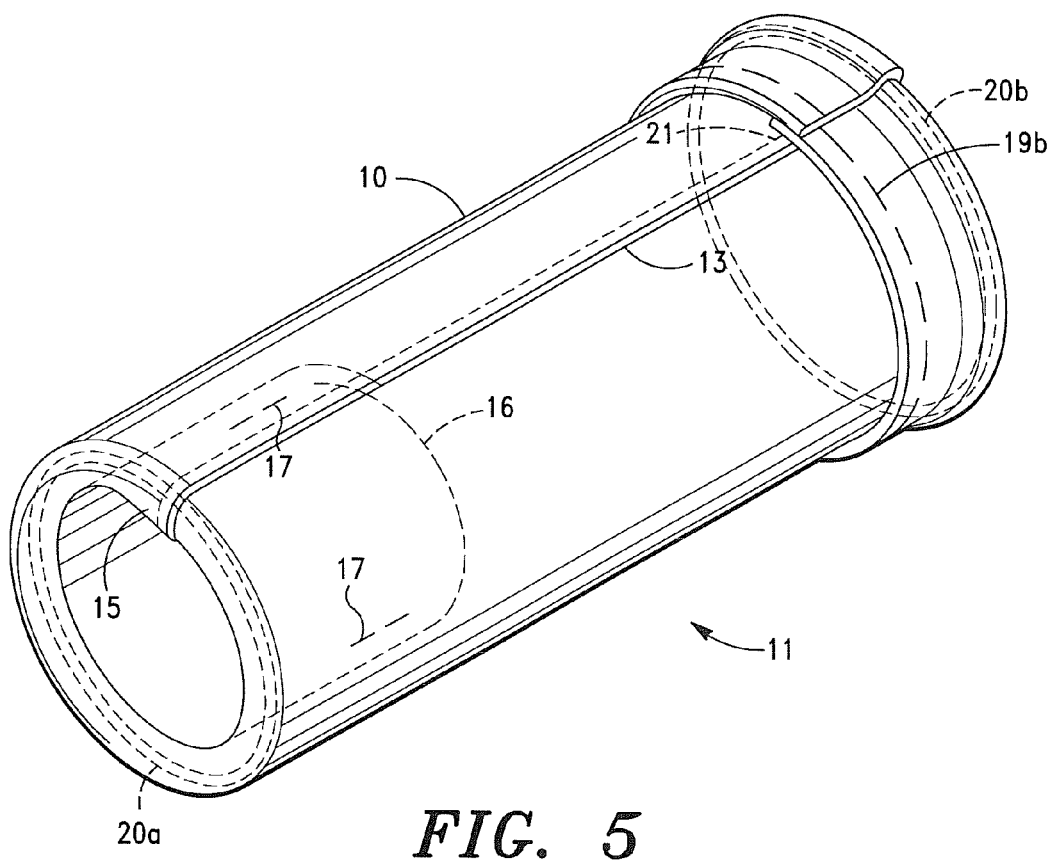
FIG. 5 is a perspective view of one embodiment of an anchored tissue valve, in accordance with the invention.

Referring now to FIG. 5, after the first and second ends 16, 18 of the ECM sheet 10 are sutured, the first side 13 of the ECM sheet 10 is rolled to meet the second side 15 of the sheet to form a substantially tubular structure, i.e. tubular anchored tissue valve 11. As will readily be apparent to one having ordinary skill in the art, alternatively, the second side 15 of the sheet can be rolled to meet the first side 13 of the sheet 10 to form the tubular valve structure.

Figure 6:
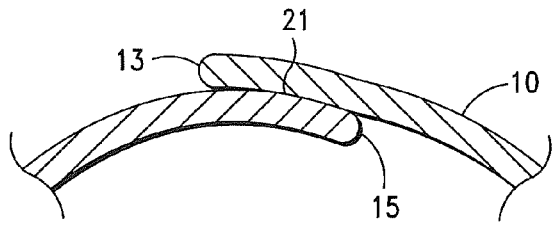
FIG. 6 is a partial front (or end) plan, sectional view of the anchored tissue valve shown in FIG. 5, showing the joined or sutured sides of the support member, in accordance with the invention.
Figure 7:
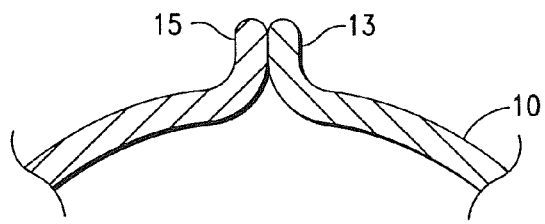
FIG. 7 is a partial front plan, sectional view of an end of an anchored tissue valve showing another embodiment of sutured sides of the support member, in accordance with the invention.

As shown in FIGS. 5 and 6, in some embodiments of the invention, one of the sheet sides, e.g., side 13, overlaps the other side, e.g., side 15. In some embodiments, the first and second sides 13, 15 abut, as shown in FIG. 7.

After the sheet sides 13, 15 are joined, the sides 13, 15 are similarly sutured 21. According to the invention, the sutures 21 can similarly comprise spaced sutures or a continuous suture.

Referring now to FIG. 8, there is shown a side plan, sectional view of the anchored tissue valve 11 described above. As illustrated in FIG. 8, the first anchoring mechanism (or anchor) 20a is disposed within the sheet pocket 23 that is formed by folding the first end 16 of the ECM sheet 10 over. The second anchoring mechanism (or anchor) 20b is disposed in the sheet pocket 25 that is formed by folding the second end 18 of the sheet 10 over.

Figure 10:
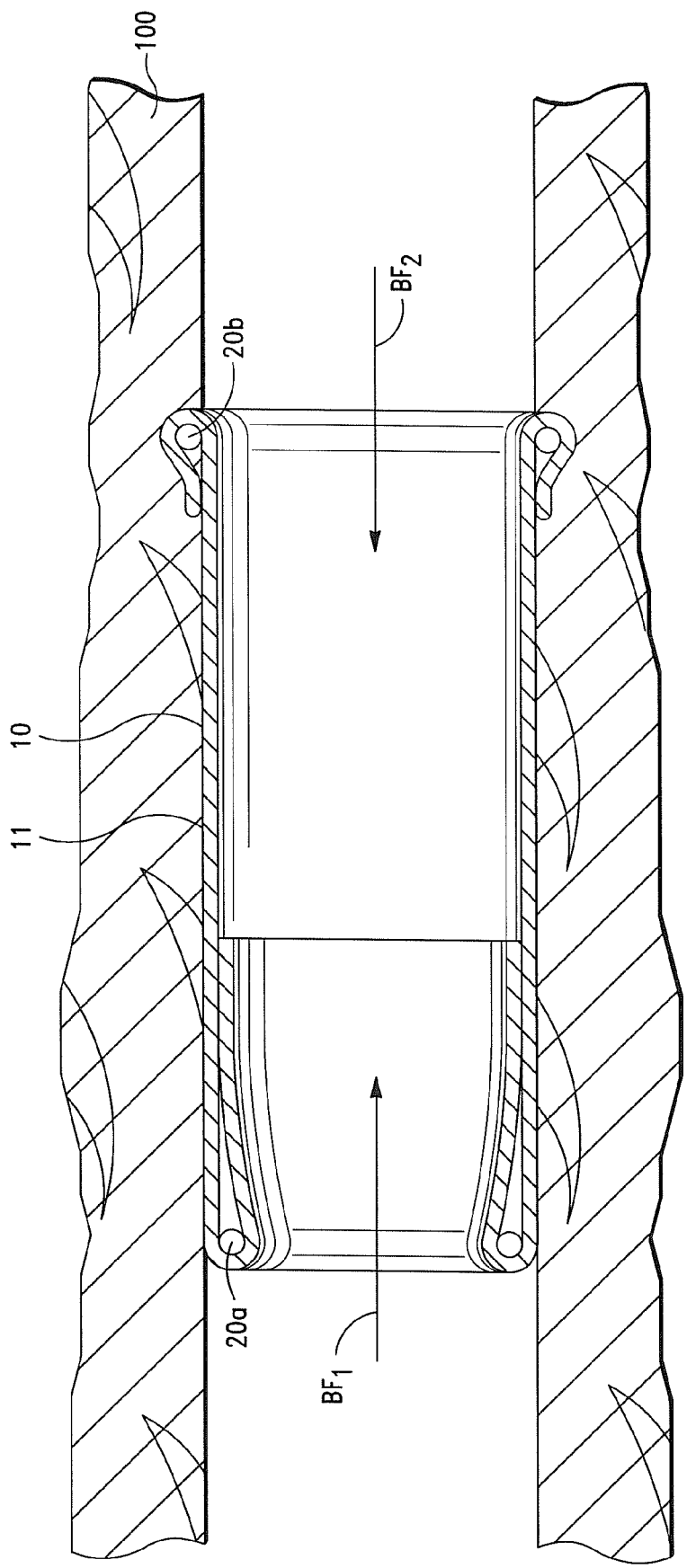
FIG. 10 is a side plan, sectional view of the anchored tissue valve shown in FIG. 8 implanted in a cardiovascular vessel, in accordance with the invention.

Referring now to FIG. 10, there is shown is a side plan, sectional view of the anchored tissue valve 11 in a post-deployment configuration in a cardiovascular vessel 100, wherein the valve 11 (and/or ECM support member 10) is disposed proximate host tissue of the vessel 100.

According to the invention, the anchored tissue valve 11 can be deployed in a cardiovascular vessel by various traditional or minimally invasive means.

Figure 9:
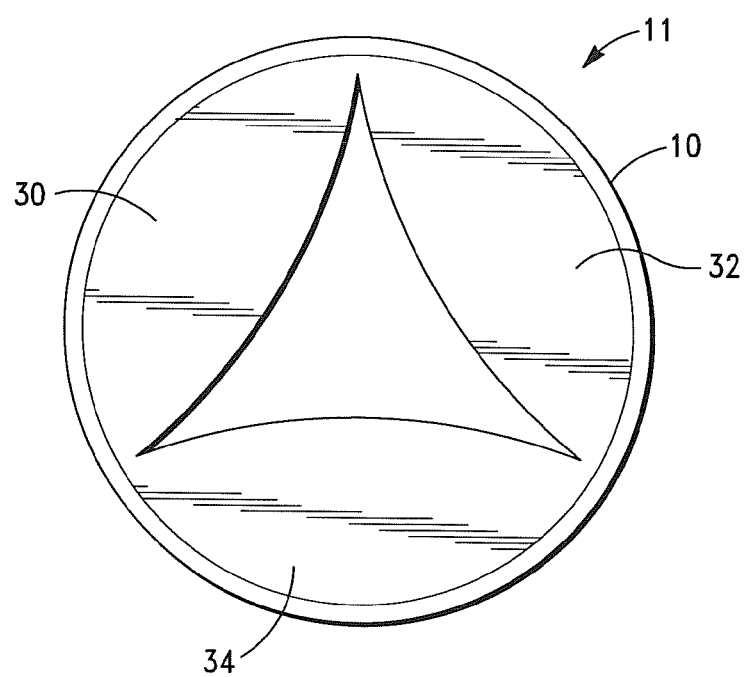
FIG. 9 is a front (or end) plan view of a proximal end of the anchored tissue valve shown in FIG. 8, showing the leaflets formed by blood flow (i.e. regurgitating blood) therethrough, in accordance with the invention.

When deployed in a cardiovascular vessel, the anchored tissue valve 11 allows normal blood flow therethrough in the direction denoted by Arrow "$BF_1$" and selectively restricts regurgitation of blood in the direction denoted by Arrow $BF_2$, i.e. the leaflets 30, 32 and 34 formed by suturing the first end 16 of the ECM sheet to the inner surface of the formed tubular valve structure (or member 10) expand and restrict fluid flow therethrough (see FIG. 9).

According to the invention, the leaflets 30, 32, 34 can have various shapes and sizes, such as shown in U.S. Pat. No. 8,257,434 and Co-pending application Ser. No. 13/560,573, which are incorporated by reference herein.

The shape and length of each leaflet 30, 32, 34, i.e. valve structure, is, of course, dependent upon the suturing points of the support member end 16 and the size, i.e. operative diameter, of the tubular support member and, hence, valve formed therefrom.

In some embodiments of the invention, the leaflets 30, 32, 34 have a substantially triangular shape.

Referring now to FIGS. 11-15, another embodiment of an anchored tissue valve of the invention will be described in detail. In a preferred embodiment of the invention, the anchored tissue valve 40 similarly includes a support member 10 with at least one internal leaflet and at least one anchoring mechanism, more preferably, at least two anchoring mechanisms (denoted "42a" and "42b" in FIG. 15).

In a preferred embodiment, the support member 10 similarly comprises an expandable ECM material that is capable of transitioning from a pre-deployment configuration, wherein the support member, i.e. ECM material, and, hence, anchored tissue valve formed therefrom, is capable of being positioned within a cardiovascular vessel, to a post-deployment configuration, wherein the anchored tissue valve is disposed proximate host tissue of the vessel.

In a preferred embodiment of the invention, the anchoring mechanisms 42a, 42b comprise expandable anchoring mechanisms (or anchors) that facilitate the noted pre-deployment configuration of the support member 10 and are similarly capable of transitioning from a pre-deployment configuration to a post-deployment configuration, wherein the support member 10 and, hence anchored valve formed therefrom, is positioned proximate host tissue of the vessel.

Figure 11:
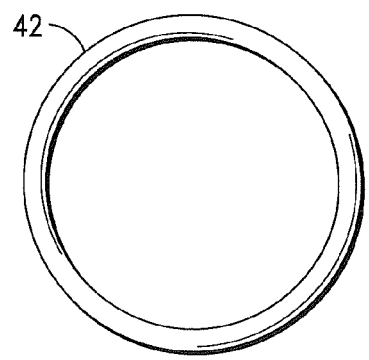
FIG. 11 is a front plan view of one embodiment of a single-ring expandable anchoring mechanism, in accordance with the invention.

As illustrated in FIG. 11, in some embodiments, the anchoring mechanisms 42a, 42b comprise single ring members.

In some embodiments of the invention, the anchoring mechanisms 42a, 42b (or rings) preferably have a thickness in the range of approximately 0.25-1.0 mm. In some embodiments, the anchoring mechanisms 42a, 42b preferably have a thickness in the range of approximately 0.05-0.25 mm.

According to the invention, the anchoring mechanisms 42a, 42b can similarly comprise various materials, preferably biocompatible materials, such as a biocompatible metal, e.g., stainless steel, and various polymeric materials. The anchoring mechanisms 42a, 42b can also comprise various biodegradable materials, such as magnesium.

Thus, in some embodiments, the anchoring mechanisms 42a, 42b comprise stainless steel.

In some embodiments, the anchoring mechanisms 42a, 42b comprise a cobalt-chrome nickel alloy.

In some embodiments, the anchoring mechanisms 42a, 42b comprise magnesium or an alloy thereof.

In some embodiments of the invention, the anchoring mechanisms 42a, 42b comprise a biocompatible shape memory alloy, including, without limitation, Nitinol®.

As stated above, in some embodiments of the invention, the metal anchoring mechanisms 42a, 42b include a coating of an immunomodulating compound that suppresses acute immune responses, while up-regulating chronic immune response (i.e. tissue reconstruction).

In some embodiments of the invention, the anchoring mechanisms 42a, 42b comprise a polymeric material, more preferably, a biocompatible and biodegradable polymeric material, such as, without limitation, polyesters, poly(amino acids), polyanhydrides, polyorthoesters, polyurethanes, polycarbonates, homopolymers and copolymers of polylactic acid) and poly(glycolic acid), copolyesters of e-caprolactone, trimethylene carbonate, and para-dioxanone, and like polymeric materials.

According to the invention, the anchoring mechanisms 42a, 42b can similarly comprise a cross-linked ECM material.

According to the invention, the anchored tissue valve 40 (shown in FIGS. 14 and 15) is formed as follows: First, the sides of the support member or ECM sheet 10 are joined, as discussed above.

After the sides of the ECM sheet 10 are joined, the first end 16 of the sheet 10 is folded over inwardly. A first anchoring mechanism (denoted "42a") is then positioned in the pocket 23 formed by the folded over first sheet end 16.

After the first anchoring mechanism 42a is positioned in the sheet pocket 23, the first end 16 of the ECM sheet 10 is similarly sutured to the top surface at three, preferably, equally spaced positions to form the valve leaflets 30, 32, 34 (see FIG. 9).

A second anchoring mechanism "42b" is then positioned proximate the second sheet end 18. In some embodiments, the second sheet end 18 is then folded over to encase the second anchoring mechanism 42b in the pocket 25 formed by the folded over end 18. The second sheet end 18 is then sutured to the ECM sheet surface.

In some embodiments of the invention, the proximal ends of the anchoring mechanisms 42a, 42b (denoted "45a" and "45b" in FIGS. 12 and 13) are also sutured to the ECM sheet 10 to maintain the position of the anchoring mechanisms 42a, 42b in respective sheet pockets 23 and 25 (see FIG. 15).

As indicated, in a preferred embodiment of the invention, the anchoring mechanisms 42a, 42b are capable of transitioning from a pre-deployment configuration, wherein the pre-deployment configuration of the support member 10 and, hence, tissue valve 40 is similarly facilitated, to a post-deployment configuration, wherein at least the proximal and distal ends of the tissue valve 40 are supported and positioned proximate the wall of a vessel (i.e. host tissue thereof) by the anchoring mechanisms 42a, 42b.

In some embodiments of the invention, the primary function of the anchoring mechanisms 42a, 42b (and expandable anchoring mechanisms 52a, 52b, 62a, 62b, and 72a and 72b, discussed below) is to position the anchored tissue valve 40 (and tissue valves 50, 60 and 70) proximate host tissue of a cardiovascular vessel, and maintain contact therewith, for a predetermined temporary anchor support time period.

In some embodiments, wherein the support member 10 comprises an ECM material, the temporary anchor support time period is within the process of tissue regeneration.

Thus, in some embodiments of the invention, the anchor support time period is within the range of approximately 12-36 months. In some embodiments, the anchor support time period is within the range of approximately 3-12 months. In some embodiments, the anchor support time period is within the range of approximately 1-3 months.

According to the invention, the anchor support time period can also be modulated.

In some embodiments of the invention, the anchoring mechanisms 42a, 42b (and expandable anchoring mechanisms 52a, 52b, 62a, 62b, and 72a and 72b) completely degrade after the anchor support time period.

In some embodiments of the invention, degradation of anchoring mechanisms 42a, 42b (and expandable anchoring mechanisms 52a, 52b, 62a, 62b, and 72a and 72b) is further controlled, whereby substantially all of the anchoring mechanisms material is absorbed proximate the ECM support member 10. According to the invention, the noted controlled degradation is achieved by defined member thicknesses and supporting forces exerted on the ECM support member 10 by the anchoring mechanisms 42a, 42b (and expandable anchoring mechanisms 52a, 52b, 62a, 62b, and 72a and 72b), and the remodeling characteristics effectuated by the ECM support member 10 (or material thereof), whereby, when an anchored tissue valve is deployed in a vessel, i.e. the ECM support member 10 and anchoring mechanisms 42a, 42b (or expandable anchoring mechanisms 52a, 52b, 62a, 62b, and 72a and 72b) are in a post-deployment configuration), new tissue is generated and encases the anchoring mechanisms 42a, 42b (and expandable anchoring mechanisms 52a, 52b, 62a, 62b, and 72a and 72b). The anchoring mechanism material is then absorbed while encased by the new tissue, which substantially reduces or eliminates the possibility of anchoring mechanism fragments flowing into and obstructing a vessel.

In some embodiments of the invention, degradation of the anchoring mechanisms 42a, 42b (and expandable anchoring mechanisms 52a, 52b, 62a, 62b, and 72a and 72b) is controlled, whereby the anchoring mechanisms 42a, 42b (and expandable anchoring mechanisms 52a, 52b, 62a, 62b, and 72a and 72b) are encased (or enclosed) in an endothelial lining after tissue remodeling commences for a defined period of time during and post healing, which similarly substantially reduces or eliminates the possibility of the anchor fragments flowing into and obstructing a vessel.

As illustrated in FIG. 11 (and shown in FIG. 15), each anchoring mechanism 42a, 42b preferably has a substantially circular "post-deployment" configuration or shape, i.e. shape after placement in a vessel. To facilitate deployment of the anchored tissue valve 40 into a cardiovascular vessel, each anchoring mechanism 42a, 42b also has a predetermined initial or "pre-deployment" configuration or shape.

Figure 12:
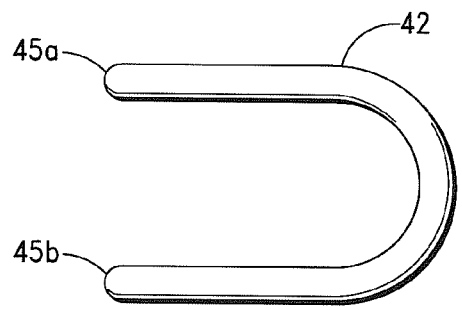
FIG. 12 is a side plan view of the single-ring anchoring mechanism shown in FIG. 11 in a pre-deployment configuration, in accordance with the invention.
Figure 13:
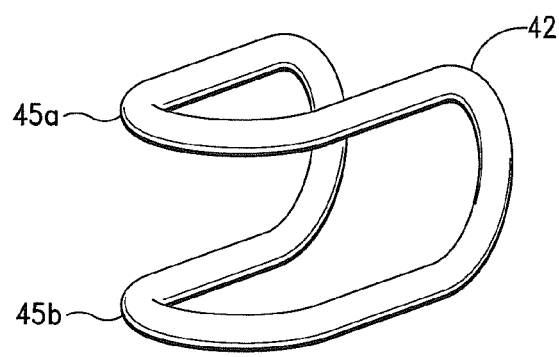
FIG. 13 is a perspective view of the single-ring anchoring mechanism shown in FIG. 11 in a pre-deployment configuration, in accordance with the invention.

As discussed in detail below, the initial or pre-deployment configuration is dependent upon the anchor material. Thus, in some embodiments of the invention, each anchoring mechanism 42a, 42b is formed with a pre-deployment configuration, such as shown in FIGS. 12 and 13.

In some embodiments of the invention, each anchoring mechanism 42a, 42b is formed with a substantially circular shape, such as shown in FIG. 11. The anchoring mechanisms 42a, 42b are then re-configured (via mechanical force means) to achieve the pre-deployment configuration shown in FIGS. 12 and 13.

As indicated above, in some embodiments of the invention, the anchoring mechanisms 42a, 42b comprise a biocompatible metal, including, without limitation, stainless steel and magnesium. The metal can also comprise a cobalt-chrome-nickel alloy.

In these embodiments, the anchoring mechanisms 42a, 42b are initially formed in a pre-deployment configuration. In a preferred embodiment of the invention, the pre-deployment configuration similarly comprises a substantially saddle shape, such as shown in FIGS. 12 and 13. As illustrated in FIG. 14, the noted shape reduces the effective diameter of the valve 40, i.e. places the valve 40 in a pre-deployment configuration, which allows the anchored valve 40 to be easily placed in a vessel 100.

After the anchored tissue valve 40 is placed at a desired position within the vessel 100, the valve 40 is expanded, e.g. via a balloon, whereby anchoring mechanisms 42a, 42b are plastically deformed (i.e. re-configured or expanded) to achieve a substantially circular (and permanent) shape (see FIG. 15), and whereby anchoring mechanisms 42a, 42b position the ECM support member 10, and, hence, tissue valve 40 proximate host tissue of the vessel.

In some embodiments of the invention, the anchoring mechanisms 42a, 42b comprise a biocompatible shape memory alloy, including, without limitation, Nitinol®. In these embodiments, the anchoring mechanisms 42a, 42b are initially formed in a substantially circular pre-deployment configuration or shape and subsequently heat-treated at a first temperature (i.e. shape set heat treatment).

The anchoring mechanisms 42a, 42b are then deformed or formed in a pre-deployment configuration or shape. In a preferred embodiment of the invention, the pre-deployment configuration or shape comprises a substantially saddle shape, such as shown in FIGS. 12 and 13.

As is well known in the art, when the temperature of the anchoring mechanisms 42a, 42b reach and exceed the Nitinol® transition temperature (i.e. stress induced martensitic structure)—normally prior to deployment in a vessel—the anchoring mechanisms 42a, 42b recover (or expand to) their original circular shape, whereby each anchoring mechanism 42a, 42b exerts a supporting force on the ECM support member 10 to position the ECM support member 10, and, hence, tissue valve 40 proximate host tissue of the vessel.

Referring now to FIGS. 16 and 17, there is shown another embodiment of an expandable anchoring mechanism 52. As illustrated in FIG. 16, the expandable anchoring mechanism 52 includes at least one helically arranged band element 54 forming a tubular configuration; the band element 54 comprising a plurality of uniformly shaped closed, interconnecting cells 56, and a plurality of connector elements extending between and interconnecting longitudinally spaced portions of the band over its tubular length.

According to the invention, the cells 56 can comprise various shapes, such a rectangular and diamond shape. In the embodiment shown in FIGS. 16 and 17, the cells 56 are diamond shaped.

According to the invention, the anchored tissue valve 50 (shown in FIG. 18) is similarly formed as follows: First, the sides of the ECM support member 10 are joined, as discussed above.

After the sides of the ECM support member 10 are joined, the first end 16 of the support member 10 is folded over inwardly. A first anchoring mechanism (denoted "52a") is then positioned in the pocket 23 formed by the folded over first support member end 16.

After the first anchoring mechanism 52a is positioned in the sheet or member pocket 23, the first end 16 of the ECM support member 10 is similarly preferably sutured to the top surface at three, preferably, equally spaced positions to form the valve leaflets 30, 32, 34 (see FIG. 9).

Figure 18:
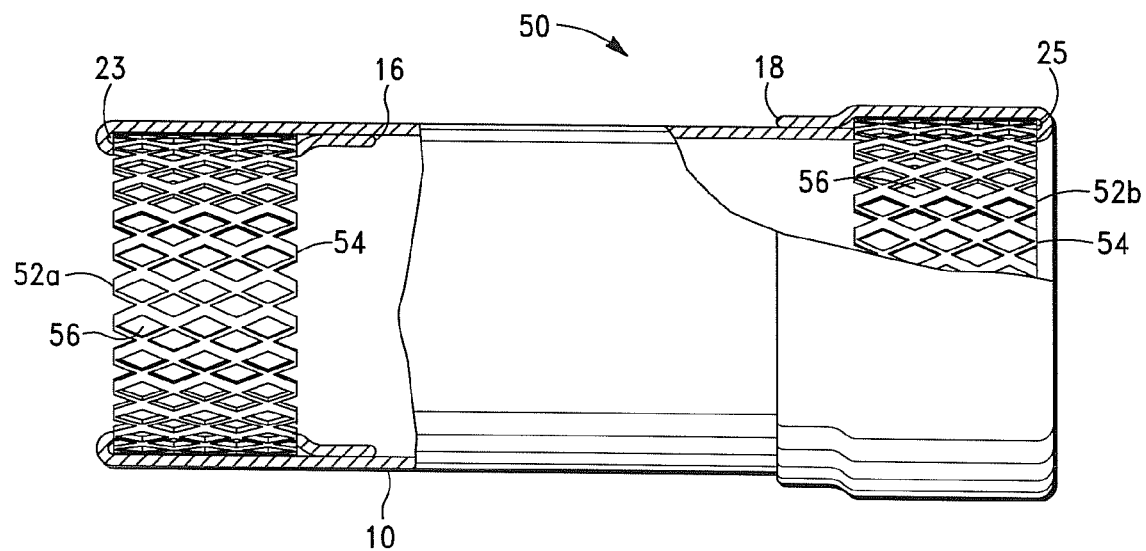
FIG. 18 is a side plan, partial sectional view of one embodiment of an anchored valve having the expandable multi-cell anchoring mechanism shown in FIG. 17, in accordance with the invention.

In some embodiments of the invention, after the first end 16 of the ECM sheet 10 is folded over, the sheet is similarly sutured proximate the first anchoring mechanism 52a to maintain the position of the anchoring mechanism 52a within the sheet pocket 23 (see FIG. 18).

A second anchoring mechanism (denoted "52b") is then positioned proximate the second support member end 18. In some embodiments, the second support member end 18 is then folded over outwardly to encase the second anchoring mechanism 52b in the pocket 25 formed by the folded over end 18. The second support member end 18 is then sutured to the ECM sheet surface.

In a preferred embodiment of the invention, the anchoring mechanisms 52a, 52b are similarly capable of transitioning from a first pre-deployment configuration, wherein a pre-deployment configuration of anchored tissue valve 50 is facilitated, i.e. a configuration that allows the valve 50 to be positioned within a cardiovascular vessel, to a first post-deployment configuration, wherein at least the proximal and distal ends of the tissue valve 50 are supported and positioned proximate the wall of the vessel (i.e. host tissue thereof) by the anchoring mechanisms 52a, 52b.

According to the invention, the anchoring mechanisms 52a, 52b can similarly comprise various materials, preferably biocompatible materials, such as a biocompatible metal, e.g., stainless steel, and various polymeric materials. The anchoring mechanisms 52a, 52b can also comprise various biodegradable materials, such as magnesium or a magnesium alloy.

In some embodiments of the invention, the anchoring mechanisms 52a, 52b comprise a biocompatible shape memory alloy, including, without limitation, Nitinol®.

As stated above, in some embodiments of the invention, the metal anchoring mechanisms 52a, 52b include a coating of an immunomodulating compound that suppresses acute immune responses, while up-regulating chronic immune response (i.e. tissue reconstruction).

In some embodiments of the invention, the primary function of the anchoring mechanisms 52a, 52b is to similarly position the anchored tissue valve 50 proximate host tissue of a vessel, and maintain contact therewith, for a predetermined "temporary" anchor support time period.

In some embodiments of the invention, wherein the support member 10 comprises an ECM material, the anchor support time period is within the process of tissue regeneration.

As illustrated in FIG. 17, each anchoring mechanism 52a, 52b preferably has a substantially circular "post-deployment" configuration. To facilitate deployment of the anchored tissue valve 50 into a cardiovascular vessel, each anchoring mechanism 52a, 52b also has a pre-deployment configuration.

As discussed in detail below, the initial or pre-deployment configuration is similarly dependent upon the anchoring mechanism material.

As indicated above, in some embodiments of the invention, the anchoring mechanisms 52a, 52b comprise a biocompatible metal, including, without limitation, stainless steel and magnesium. The metal can also comprise a cobalt-chrome-nickel alloy.

In these embodiments, each anchoring mechanisms 52a, 52b is formed with a substantially circular "compressed" pre-deployment configuration. After the anchored tissue valve 50 is placed at a desired position within a vessel, the valve 50 is expanded, e.g. via a balloon, whereby the anchoring mechanisms 52a, 52b are plastically deformed (i.e. re-configured or expanded) to achieve an "expanded" substantially circular, post-deployment configuration (see FIG. 18), and whereby anchoring mechanisms 52a, 52b position the ECM support member 10, and, hence, tissue valve 50 proximate host tissue of the vessel, and maintain contact therewith, for a predetermined anchor support time period.

In some embodiments of the invention, the anchoring mechanisms 52a, 52b comprise a biocompatible shape memory alloy, such as Nitinol®. In these embodiments, the anchoring mechanisms 52a, 52b are initially formed in a substantially circular "expanded" pre-deployment configuration or shape and subsequently heat-treated at a first temperature (i.e. shape set heat treatment).

The anchoring mechanisms 52a, 52b are then similarly deformed or formed in a "compressed" pre-deployment configuration or shape.

When the temperature of the anchoring mechanisms 52a, 52b reach and exceed the Nitinol® transition temperature (i.e. stress induced martensitic structure) the anchoring mechanisms 52a, 52b recover (or expand to) their original circular shape, whereby each anchoring mechanism 52a, 52b similarly exerts a supporting force on the ECM support member 10 to position the ECM support member 10, and, hence, tissue valve 50 proximate host tissue of the vessel.

Referring now to FIGS. 19-22, there is shown another embodiment of an expandable anchoring mechanism 62. As illustrated in FIGS. 19 and 20, in some embodiments, the anchoring mechanism 62 comprises an expandable band 64.

Figure 23:
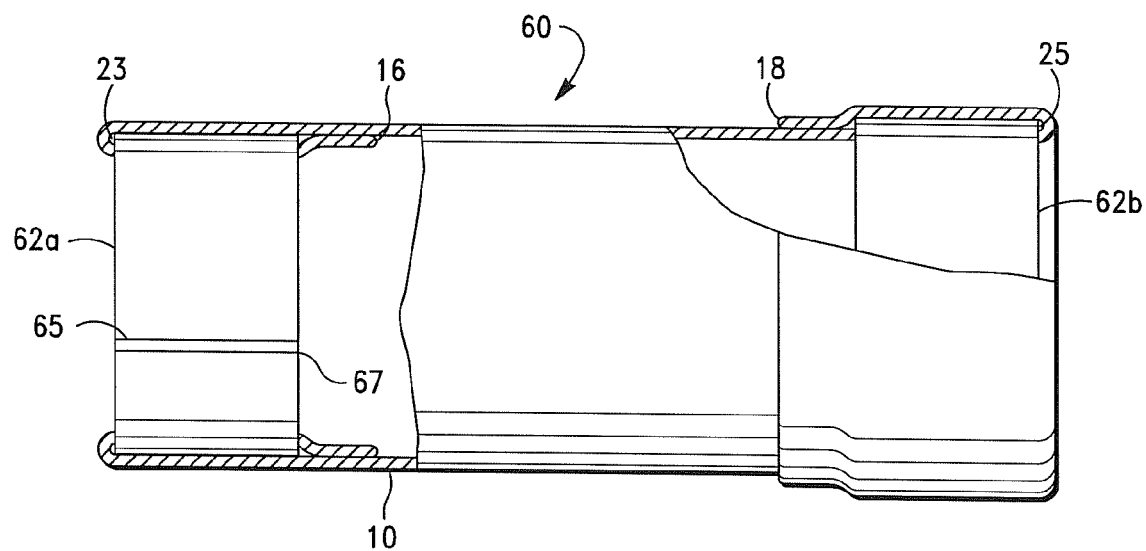
FIG. 23 is a side plan, partial sectional view of one embodiment of an anchored valve having the expandable anchoring mechanism shown in FIG. 19, in accordance with the invention.
Figure 24:
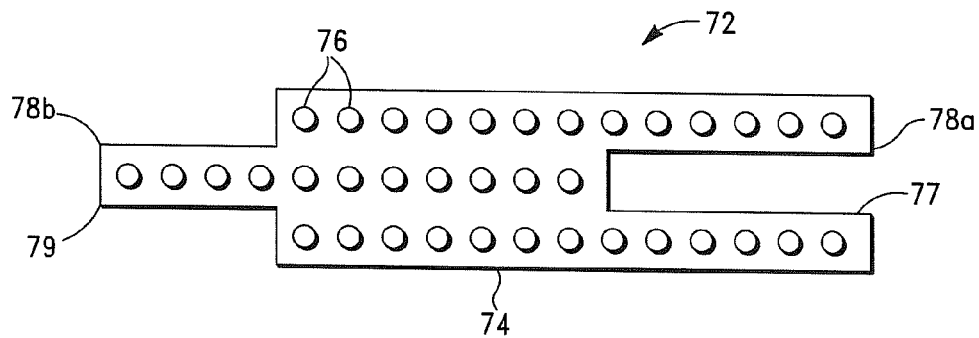
FIG. 24 is a top plan view of another embodiment of an expandable anchoring mechanism, in accordance with the invention.

Referring now to FIG. 23, there is shown one embodiment of an anchored valve 60. As illustrated in FIG. 23, the anchored valve 60 includes a first expandable anchoring mechanism (or band) 62a disposed proximate the first end 16 of the support member 10 and a second expandable anchoring mechanism 62b disposed proximate the second end 18 of the member 10.

According to the invention, the anchored valve 60 is formed in a manner similar to the formation of anchored tissue valve 50, discussed above.

In a preferred embodiment of the invention, the expandable anchoring mechanisms or bands 62a, 62b are similarly capable of transitioning from a pre-deployment configuration (see FIG. 21), wherein the pre-deployment configuration of the support member 10 and, hence, anchored tissue valve 60 formed therefrom is facilitated, to a post-deployment configuration (see FIG. 20), wherein at least the proximal and distal ends of the tissue valve 60 are positioned proximate the wall of the vessel (i.e. host tissue thereof) by the anchoring mechanisms 62a, 62b.

According to the invention, the anchoring mechanisms 62a, 62b can similarly comprise various materials, preferably biocompatible materials, such as a biocompatible metal, e.g., stainless steel, and various polymeric materials. The anchoring mechanisms 62a, 62b can also comprise various biodegradable materials, such as magnesium or a magnesium alloy.

In some embodiments of the invention, the anchoring mechanisms 62a, 62b comprise a biocompatible shape memory alloy, including, without limitation, Nitinol®.

As stated above, the metal anchoring mechanisms 62a, 62b can also include a coating of an immunomodulating compound that suppresses acute immune responses, while up-regulating chronic immune response (i.e. tissue reconstruction).

To facilitate the pre-deployment configuration and transition to the post-deployment configurations of the anchoring mechanisms 62a, 62b, the anchoring mechanisms 62a, 62b comprise discontinuous bands. As illustrated in FIGS. 21 and 22, the discontinuous bands are designed and configured, whereby a first end of anchoring mechanism 65 over-laps the second end of the anchoring mechanism 67 to facilitate a "compressed" pre-deployment configuration.

The pre-deployment configuration is similarly dependent upon the anchor material.

As indicated above, in some embodiments of the invention, the anchoring mechanisms 62a, 62b comprise a biocompatible metal, including, without limitation, stainless steel and magnesium. The anchoring mechanisms 62a, 62b can also comprise a cobalt-chrome-nickel alloy.

In these embodiments, each anchoring mechanism 62a, 62b is formed with a substantially circular "compressed" pre-deployment configuration or shape, such as shown in FIGS. 21 and 22. After the anchored tissue valve 60 is placed at a desired position within a vessel, the valve 60 is expanded, whereby the anchoring mechanisms 62a, 62b expand to achieve the "expanded" substantially circular, post-deployment configuration shown in FIGS. 20 and 23, and whereby the anchoring mechanisms 62a, 62b position the ECM support member 10, and, hence, tissue valve 60 proximate host tissue of the vessel.

According to the invention, anchoring mechanisms 62a, 62b can similarly comprise a biocompatible shape memory alloy, such as Nitinol®. In these embodiments, the anchoring mechanisms 62a, 62b are initially formed in the "expanded" pre-deployment configuration and subsequently heat-treated at a first temperature (i.e. shape set heat treatment).

The anchoring mechanisms 62a, 62b are then similarly deformed or formed in a "compressed" pre-deployment configuration or shape.

When the temperature of the anchoring mechanisms 62a, 62b reach and exceed the Nitinol® transition temperature (i.e. stress induced martensitic structure) the anchoring mechanisms 62a, 62b recover (or expand to) their original circular shape, whereby each anchoring mechanism 62a, 62b similarly exerts a supporting force on the ECM support member 10 to position the ECM support member 10, and, hence, tissue valve 60 proximate host tissue of the vessel.

As indicated above, in some embodiments of the invention, the anchoring mechanisms comprise microneedle anchoring mechanisms having plurality of biodegradable microneedles or barbs that are adapted to maintain contact of the ECM member 10 and, hence, anchored valve formed therefrom against the wall of a vascular structure when disposed therein.

Suitable microneedle anchoring members are disclosed in Co-Pending application Ser. No. 13/686,131, filed Nov. 27, 2012; which is incorporated by reference herein in its entirety.

According to the invention, various shaped microneedles or barbs can be employed within the scope of the invention; provided, the microneedle or barb has a head (or head region) that is able to pierce tissue and remain engaged to the tissue for a predetermined period of time.

In some embodiments, the microneedle anchoring member and, hence, microneedles comprise a biodegradable polymeric material, an ECM material or a pharmacological agent or composition (i.e. drug), e.g., Heparin®, Plavix®, etc., or a combination thereof In some embodiments, the microneedle anchoring member and, hence, microneedles comprise a biocompatible and bioabsorbable metal, such as magnesium.

In some embodiments, the microneedles comprise drug-eluting members that facilitate the direct administration of a pharmacological agent or composition to host tissue.

In some embodiments of the invention, the drug-eluting capability is facilitated by forming at least one, more preferably, each microneedle out of a pharmacological agent or composition, whereby upon engagement of the biodegradable microneedles to a recipient's tissue, the microneedles dissolve or degrade and the pharmacological agent or composition is administered to the recipient at the engagement site.

In some embodiments, the drug-eluting capability is facilitated by coating at least one, more preferably, each microneedle with a pharmacological agent or composition, whereby upon engagement of the microneedles to a recipient's tissue, the pharmacological agent or composition is absorbed and, hence, administered to the recipient.

In some embodiments of the invention, at least one, more preferably, each microneedle has an internal reservoir that is adapted to receive and contain a pharmacological agent or composition therein. According to the invention, upon engagement of the biodegradable microneedles to a recipient's tissue, the microneedles dissolve or degrade and the pharmacological agent or composition contained in the reservoir is administered to the recipient.

In some embodiments of the invention, at least one, more preferably, each microneedle has an internal reservoir that is adapted to receive and contain a pharmacological agent or composition therein and at least one, more preferably, a plurality of lumens in communication with the reservoir and, hence, pharmacological agent or composition contained therein. The microneedles also include a biodegradable or bioabsorbable coating (or sealing layer) on the outer surface to temporarily seal reservoir and inter-connected lumens. Upon engagement of the microneedles to a recipient's tissue, the coating dissolves or degrades and the pharmacological agent or composition contained in the reservoir is administered to the recipient via the microneedle lumens.

As set forth in detail in Co-Pending application Ser. No. 13/686,131, the on-set and rate of administration of a pharmacological agent or composition can be determined and regulated by, among other things, the composition and/or properties of the base microneedle, e.g. dissolution rate, size of lumens, etc., and the composition and/or properties of the pharmacological agent or composition, and sealing coatings.

Figure 25:
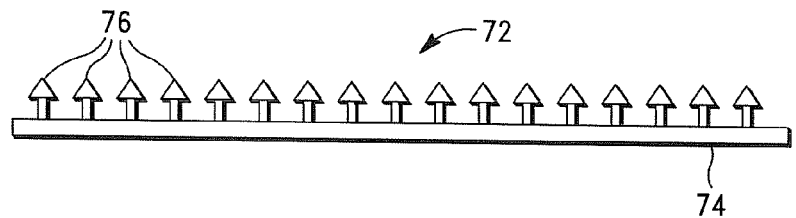
FIG. 25 is a side plan view of the anchoring mechanism shown in FIG. 24, in accordance with the invention.

Referring now to FIGS. 24, 25 26A and 26B, there is shown one embodiment of a microneedle anchoring mechanism 72. As illustrated in FIG. 25, the microneedle anchoring mechanism 72 includes a base 74 and a plurality of microneedles 76, which are designed and configured to pierce through and project out of a support member, in this embodiment, an ECM support member 10, when an anchored valve employing the microneedle anchoring mechanism 72 is deployed in a vessel.

Figure 27:
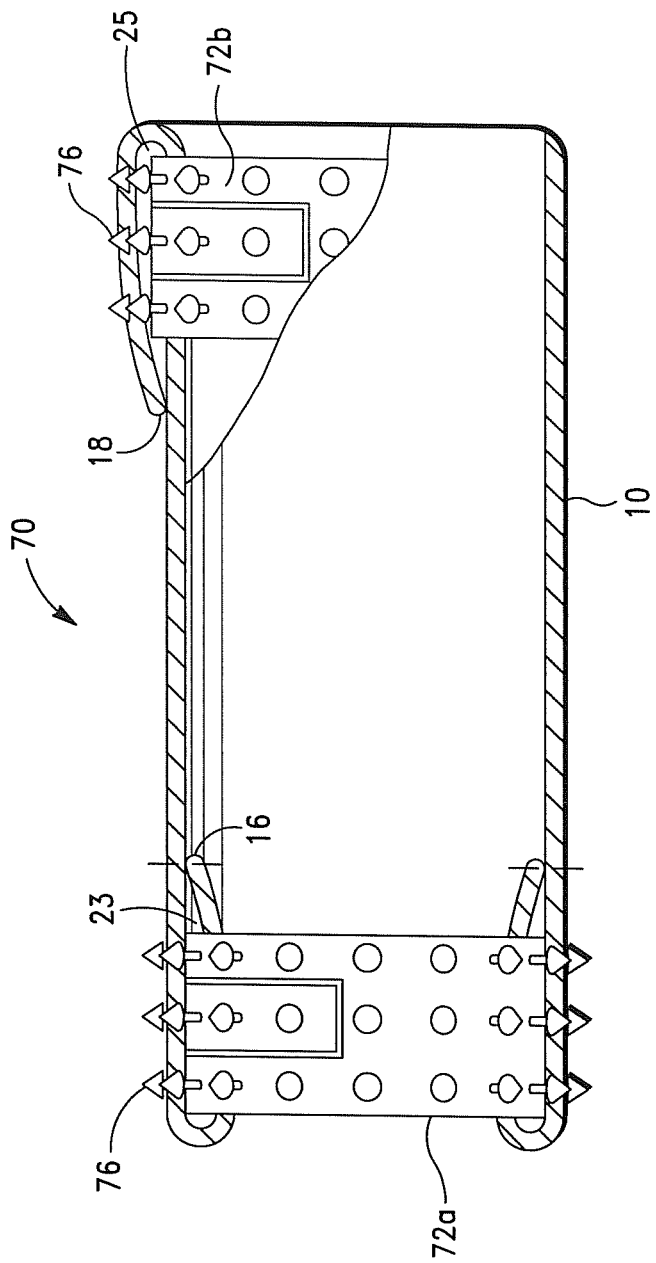
FIG. 27 is a side plan, partial sectional view of one embodiment of an anchored valve having the expandable anchoring mechanism shown in FIG. 24, in accordance with the invention.

Referring now to FIG. 27, there is shown one embodiment of an anchored valve 70 employing microneedle anchoring mechanisms 72 of the invention. As illustrated in FIG. 27, the valve 70 includes a first microneedle anchoring mechanism 72a disposed proximate the first end 16 of the support member 10 and a second microneedle anchoring mechanism 72b disposed proximate the second end 18 of the member 10.

According to the invention, the anchored tissue valve 70 is also fanned in a manner similar to the formation of anchored valves 50 and 60, discussed above.

In a preferred embodiment of the invention, the microneedle anchoring mechanisms 72a, 72b are similarly capable of transitioning from a pre-deployment configuration to facilitate a pre-deployment configuration of anchored tissue valve 70, to a post-deployment configuration, wherein at least the proximal and distal ends of the tissue valve 70 are supported and positioned proximate the wall of a vessel (i.e. host tissue thereof) by the microneedle anchoring mechanisms 72a, 72b.

Referring back to FIG. 24, to facilitate the transition of the microneedle anchoring mechanisms 72a, 72b from a pre-deployment configuration to a post-deployment configuration, a first end 78a of each microneedle anchoring mechanism base 74 includes an elongated slot 77 that is designed and configured to receive the base projection 79 on the opposing end 78b of the base 74.

Figures 26A, 26B:
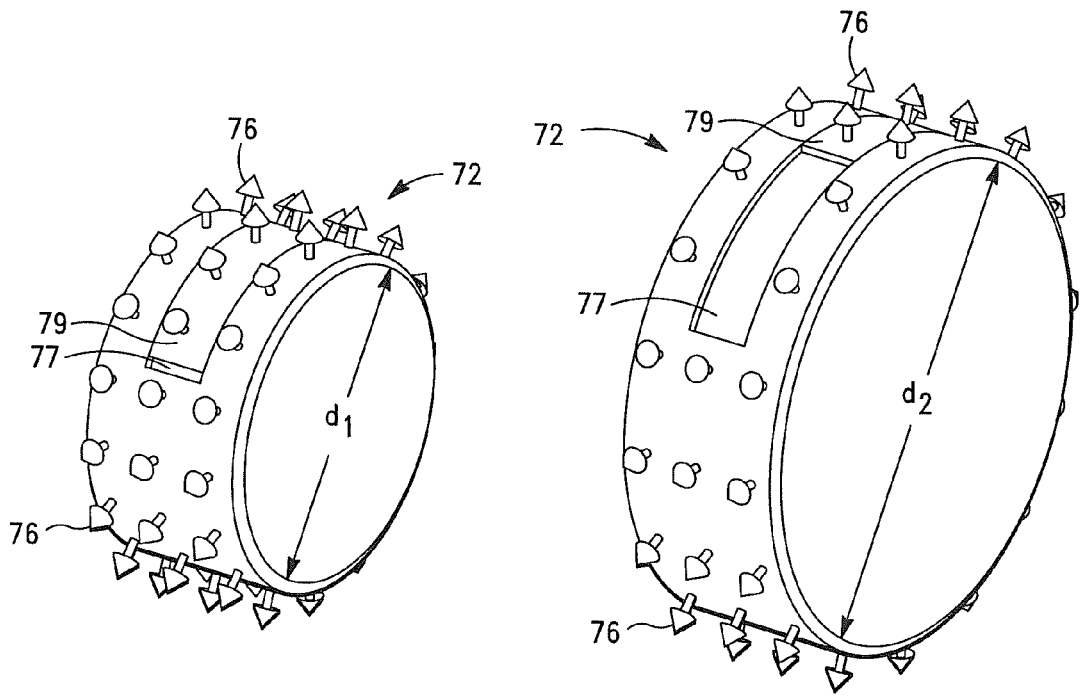
FIG. 26A is a perspective view of the expandable anchoring mechanism shown in FIG. 24 in a pre-deployment configuration, in accordance with the invention.
FIG. 26B is a perspective view of the expandable anchoring mechanism shown in FIG. 24 in a post-deployment configuration, in accordance with the invention.

Referring now to FIGS. 26A and 26B, when the microneedle anchoring mechanisms 72a, 72b are in a pre-deployment configuration, i.e. a substantially circular shape having a first diameter (denoted "$d_1$"), the elongated slot 77 slidably receives the base projection 79 therein. When the microneedle anchoring mechanisms 72a, 72b transition to a post-deployment configuration, as shown in FIG. 26B, the base projection 79 transitions (or moves) within the elongated slot 77 to facilitate an expansion (or enlargement) of the circular shape to a second larger diameter (denoted "$d_2$").

According to the invention, upon deployment of an anchored tissue valve employing the microneedle anchoring mechanisms 72a, 72b in a vessel, the microneedle anchoring mechanisms 72a, 72b position and maintain at least the ends of the support member 10 and, hence, tissue valve 70 proximate host or vessel tissue when in a post-deployment configuration. The microneedles 76 also project through tissue valve 70 and engage the vessel tissue and secure the tissue valve 70 proximate the cardiovascular vessel tissue.

As indicated above, the anchored valves of the invention can be readily employed to replace numerous valves in the body including, without limitation, diseased or defective aortic, pulmonary, mitral, tricuspid and/or peripheral venous valves.

Thus, according to the invention, the size or diameter of the anchored valves of the invention, including valves 40, 50, 60 and 70, described above, can vary to accommodate placement in various cardiovascular vessels in pediatrics and adults.

As will readily be appreciated by one having ordinary skill in the art, the present invention provides numerous advantages compared to prior art prosthetic valves. Among the advantages are the following:

The provision of improved prosthetic tissue valves that can be employed to replace diseased or defective cardiovascular valves, including peripheral venous valves.

The provision of prosthetic tissue valves that provide secure, reliable, and consistently highly effective attachment to cardiovascular vessels.

The provision of prosthetic tissue valves that include unique anchoring mechanisms that position the valves proximate target tissue for at least a pre-determined temporary period of time.

The provision of prosthetic tissue valves that exhibit optimum mechanical compatibility with vascular structures.

The provision of prosthetic tissue valves that substantially reduce or eliminate intimal hyperplasia after intervention in a vessel and the harsh biological responses associated with conventional polymeric and metal valves.

The provision of prosthetic tissue valves that induce host tissue proliferation, bioremodeling and regeneration of new tissue and tissue structures with site-specific structural and functional properties.

The provision of prosthetic tissue valves that can administer a pharmacological agent to host tissue and, thereby produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An anchored cardiovascular valve, comprising:
an expandable valve support member comprising remodelable acellular extracellular matrix (ECM) from a first mammalian tissue source, said ECM valve support member being capable of transitioning from a support member pre-deployment configuration, wherein said support member is capable of being positioned within a cardiovascular structure, to a support member post-deployment configuration, wherein said support member is disposed proximate host cardiovascular tissue of said cardiovascular structure, and wherein bioremodeling of said ECM valve support member and said host cardiovascular tissue, and regeneration of new cardiovascular tissue and cardiovascular tissue structures with site-specific structural and functional properties are induced,
said ECM valve support member having a longitudinal axis, an outer surface, a lumen, an inlet portion and an outlet portion, said lumen defining a support member inner surface, said outlet portion defining an outlet in communication with said lumen, said outlet portion being outwardly reflected over and attached to said valve support member outer surface, wherein a first anchor pocket is formed therein, said inlet portion defining an inlet in communication with said lumen, said inlet portion being inwardly reflected within said ECM valve support member lumen and attached to said support member inner surface at a first attachment point, wherein a second anchor pocket is formed therein, and wherein a first valve leaflet is formed within said ECM valve support member lumen, said valve leaflet being sized and configured to selectively restrict fluid flow through said support member; and first and second biodegradable expandable anchoring mechanisms, said first biodegradable expandable anchoring mechanism being disposed in said first anchor pocket, said second biodegradable expandable anchoring mechanism being disposed in said second anchor pocket, said first and second biodegradable anchoring mechanisms being capable of transitioning from an anchoring mechanism pre-deployment configuration, wherein said ECM valve support member is configured in said support member pre-deployment configuration, to an anchoring mechanism post-deployment configuration, wherein said first and second biodegradable expandable anchoring mechanisms temporarily position said ECM valve support member proximate said host cardiovascular tissue of said cardiovascular structure and maintain contact therewith for an anchor support period of time within said process of new cardiovascular tissue regeneration, wherein bioremodeling of said ECM valve support member and host cardiovascular tissue, and regeneration of cardiovascular tissue structures with site-specific structural and functional properties are induced, and wherein said first and second biodegradable expandable anchoring mechanisms degrade during said anchor support period of time.

2. The anchored valve of claim 1, wherein said support member inlet portion is attached to said support member inner surface at two attachment points, and wherein first and second valve leaflets are formed within said ECM valve support member lumen.

3. The anchored valve of claim 1, wherein said support member inlet portion is attached to said support member inner surface at three attachment points, and wherein first, second and third valve leaflets are formed within said ECM valve support member lumen.

4. The anchored valve of claim 3, wherein said three attachment points are positioned substantially within a common plane, said common plane being substantially perpendicular to said longitudinal axis of said ECM valve support member.

5. The anchored valve of claim 1, wherein said first tissue source is selected from the group consisting of small intestine submucosa (SIS), urinary bladder submucosa (UBS), stomach submucosa (SS), mesothelial tissue, placental extracellular matrix, ornomentum extracellular matrix, cardiac extracellular matrix, kidney extracellular matrix, pancreas extracellular matrix, and combinations thereof.

6. The anchored valve of claim 1, wherein said remodelable ECM comprises an additional pharmacological agent.

7. The anchored valve of claim 6, wherein said pharmacological agent comprises a statin selected from the group consisting of atorvastatin, cerivastatin, fluvastatin, lovastatin, mevastatin, pitavastatin, pravastatin, rosuvastatin and simvastatin.

8. The anchored valve of claim 6, wherein said pharmacological agent comprises a growth factor selected from the group consisting of transforming growth factor alpha (TGF-alpha), transforming growth factor beta (TGF-beta), fibroblast growth factor-2 (FGF-2), basic fibroblast growth factor (bFGF) and vascular epithelial growth factor (VEGF).

9. The anchored valve of claim 6, wherein said pharmacological agent comprises an anti-arrhythmic agent selected from the group consisting of quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

10. The anchored valve of claim 1, wherein said first and second biodegradable expandable anchoring mechanisms comprise a biodegradable polymeric material selected from the group consisting of a copolymer of polylactic acid and copolyesters of e-caprolactone.

11. The anchored valve of claim 1, wherein said first and second biodegradable expandable anchoring mechanisms comprise magnesium.

12. The anchored valve of claim 1, wherein said first and second biodegradable expandable anchoring mechanisms comprise crosslinked ECM from a second mammalian tissue source selected from the group consisting of SIS, UBS, SS, mesothelial tissue, ornomentum extracellular matrix, cardiac extracellular matrix, kidney extracellular matrix, pancreas extracellular matrix, lung extracellular matrix, and combinations thereof.

* * * * *